United States Patent
Bautz

(10) Patent No.: US 8,231,003 B2
(45) Date of Patent: Jul. 31, 2012

(54) PROTECTED FILTER UNITS FOR SAFETY FILTRATION AND METHOD FOR PRODUCTION THEREOF

(75) Inventor: Rainer Bautz, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 140 days.

(21) Appl. No.: 12/448,711

(22) PCT Filed: Jan. 16, 2008

(86) PCT No.: PCT/EP2008/000272
§ 371 (c)(1),
(2), (4) Date: Jul. 2, 2009

(87) PCT Pub. No.: WO2008/089900
PCT Pub. Date: Jul. 31, 2008

(65) Prior Publication Data
US 2010/0059403 A1     Mar. 11, 2010

(30) Foreign Application Priority Data
Jan. 26, 2007   (DE) .......................... 10 2007 004 114

(51) Int. Cl.
*B65D 81/20* (2006.01)
*B65B 31/00* (2006.01)

(52) U.S. Cl. ................. 206/524.8; 206/439; 206/484.1; 53/405; 53/408; 53/425; 53/434

(58) Field of Classification Search .............. 206/438, 206/439, 484.1, 484.2, 524.8; 53/403, 405, 53/407, 408, 425, 426, 432, 434, 449, 469; 422/292, 294; 210/493.5
See application file for complete search history.

(56) References Cited

U.S. PATENT DOCUMENTS

| | | | | |
|---|---|---|---|---|
| 3,613,879 | A | * | 10/1971 | Kemble .................... 206/524.8 |
| 4,603,538 | A | * | 8/1986 | Shave ............................ 53/425 |
| 4,662,521 | A | | 5/1987 | Moretti |
| 4,709,819 | A | * | 12/1987 | Lattuada et al. ........... 206/524.8 |
| 4,714,595 | A | * | 12/1987 | Anthony et al. ............... 422/294 |
| 4,727,705 | A | * | 3/1988 | Zahka ........................... 53/425 |
| 4,813,210 | A | * | 3/1989 | Masuda et al. ................. 53/425 |
| 6,705,061 | B1 | * | 3/2004 | Porret et al. ..................... 53/425 |
| 2004/0144255 | A1 | * | 7/2004 | Lersch et al. ...................... 96/69 |
| 2005/0241981 | A1 | * | 11/2005 | Gupta et al. ............... 206/524.8 |

FOREIGN PATENT DOCUMENTS

| | | |
|---|---|---|
| DE | 2 217 793 | 10/1972 |
| DE | 2837 127 C2 | 3/1979 |
| DE | 30 14 026 C2 | 3/1981 |
| DE | 44 28 291 A1 | 2/1996 |
| DE | 299 08 080 U1 | 9/1999 |
| DE | 2004 012 636 A1 | 10/2005 |
| EP | 1 520 795 A1 | 4/2005 |
| EP | 1 529 539 A1 | 5/2005 |
| WO | WO 87/05278 | 9/1987 |

* cited by examiner

*Primary Examiner* — Luan K Bui
(74) *Attorney, Agent, or Firm* — Gerald E. Hespos; Michael J. Porco

(57) ABSTRACT

The invention relates to protected filter units for safety filtration, in which the filter units are at least double-packed with different packaging materials and to a method for producing the protected filter units. In this case, the first packaging material is permeable to gases but impermeable to microorganisms and the at least second packaging material is impermeable to gases. The first packaging material fixes the at least one filter unit, and so no abrasion can take place during transport and handling. The filter units according to the invention are suitable for sterile filtration processes and for filtration processes under clean-mom conditions.

8 Claims, 1 Drawing Sheet

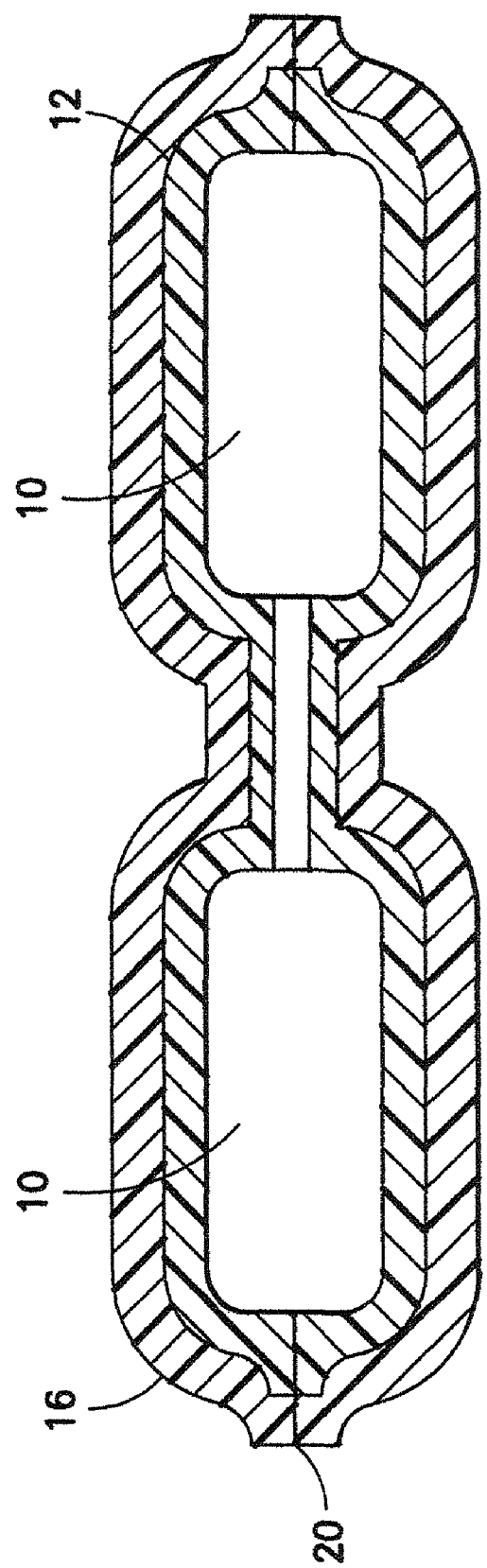

PROTECTED FILTER UNITS FOR SAFETY FILTRATION AND METHOD FOR PRODUCTION THEREOF

BACKGROUND OF THE INVENTION

1. Field of the Invention

The invention relates to protected filter units for safety filtration, in which the filter units with different packaging material are packaged at least twice, and a method for producing the protected filter units.

2. Description of the Related Art

Filter units are intended to be understood to be filter materials which in general are attached to filter material holders. Examples include prefabricated hollow-fiber filters and flat filters, filter candles, filter capsules, wound modules, filter cartridges, small filters such as syringe attachments, filters with unfiltrate and/or filtrate spaces or other filter units ready for connection. Safety filtrations are intended to be understood as those filtrations for which particular safety requirements are posed, such as sterile filtrations for retaining microorganisms, in particular bacteria, or filtrations in clean rooms, where the ingress of particles into said clean rooms, including into the gaseous and liquid media to be filtered, has to be avoided.

Sterile filter units which are loosely packaged individually in flexible bags are commercially available. Thus, DE 299 08 080 U1 describes single-use filter capsules for sterile filtration, prefabricated with connectors and single-use containers, which are loosely enclosed in a packaging. It is disadvantageous that, as a result of the loose packaging, grit is generated in the sterile product packaging space during the transport and the handling of the sterile filter units before use, and undesired particles are emitted from the packaging, and from the unpacked filter units when used in clean rooms, and into the media to be filtered. DE 101 54 702 A1 describes a reusable filter module packaging for sterile-filtering filter modules in which the filter units are fixed by specially designed fixing elements. It is disadvantageous that it is not permitted to unpack the filter units in clean rooms because the latter could be contaminated by the packaging. The filter units have to first of all be removed from the packaging in a separate area which is not part of the clean room. As a result of this, protected stockpiling of the filter units in the clean room area is not possible. DE 28 37 127 C2 describes an air-tight packaging, in particular for foodstuff, which is suitable for evacuation and/or gassing. It comprises a vat-shaped container made of a material which is sufficiently stiff for being stacked one above the other and which has on its inside a gas-tight film which holds the product to be packaged and which tapers off at the top into a flange-shaped peripheral edge, it being possible to close off the container by means of a closing sheet which can be attached to the film along the peripheral edge. The film forms a flexible inner packaging for the product, which is only attached to the container at its flange-shaped peripheral edge. The intermediate space between inner packaging and container is connected to the atmosphere via ducts. The inner packaging space can be gassed and/or made into a vacuum through the ducts, the ducts subsequently being sealed. Design and handling of the packaging is complex. It is unsuitable for filter units for safety filtrations because abrasion cannot be excluded during transport between filter unit and closing sheet and between inner packaging and housing. WO 87/05278 A1 describes an apparatus for transporting sterile articles in a double vat, each vat being sealed by a cover sheet which can be pulled off a circulating flange. To assist in the cover sheet of the inner vat being pulled off, a pulling-off band which can be gripped is attached to the latter. The rigid and complex design of the double vat is disadvantageous. It is unsuitable for filter units for safety filtrations because abrasion cannot be excluded during transport between filter unit and inner vat. DE 44 28 291 A1 discloses a single packaging for articles to be sterilized, in which the packaging surrounding the articles comprises a porous paper web and an impervious plastic film which are sealed to one another such that they can be peeled. The article can be sterilized by means of the paper web. DE 30 14 026 C2 discloses a further single packaging for articles to be sterilized, in which the packaging surrounding the articles comprises two impervious plastic films which are hot sealed to one another such that they can be peeled, it being possible to detect from the transparent or opaque look of the seal whether said seal was damaged. The laid-open patent application DE 2 217 793 discloses another single packaging for articles to be sterilized, which is composed of a special plastic film which is permeable to steam-type sterilization means but impermeable to pathogenic microorganisms, at least part of its surface being composed of an open-celled micro-porous polymer film which has a weight per unit volume which is less than the weight per unit volume of the corresponding polymer film which does not have an open-celled structure.

The above-mentioned apparatuses are unsuitable for filter units for safety filtrations because abrasion during transport between filter unit and inner vat cannot be excluded and single packaging can be easily damaged and this leads to a removal of the sterility of the filter units.

It is therefore the object of the invention to propose filter units for safety filtration which are protected until use and which themselves do not constitute a source of contamination, and a method for producing the same.

SUMMARY OF THE INVENTION

According to the invention, protected filter units for safety filtrations are proposed which comprise at least one filter unit and at least two flexible packaging materials. Here, the first packaging material is gas permeable and impermeable for microorganisms, while the at least second packaging material is impermeable to gases. The first packaging material encloses the at least one filter unit and the at least second packaging material encloses at least a first packaging material with the at least one filter unit, wherein gas is removed from the protected filter units and the first packaging material fixes the at least one filter unit in normal conditions. Normal conditions are intended to be understood as, in particular, air pressure of one atmosphere and a temperature of 18° C.

Protected filter units, in which the at least second packaging material contains a number of first packaging materials with at least one enclosed filter unit—2 are preferred, 3 to 9 first packaging materials with the at least one filter unit are particularly preferred—are particularly economical. Protected filter units in which the first packaging material contains more than one filter element are particularly advantageous. By these means, a protected filter unit can be provided for the client, the filter unit number of which being matched to the latter's specific application, for example to the number of filter candles with which a multiple filter housing is to be equipped. If high mechanical safety is important, a third flexible packaging material is present as an outer packaging.

As a result of the presence of a partial vacuum in the protected filter unit, the flexible packaging materials lie closely against the filter unit so that the filter unit can no longer be moved relative to the first packaging material and the first packaging material can no longer be moved relative to the at least second packaging material. Thus, abrasion of material of the filter unit or the packaging materials is prevented. As a result of, on the one hand, the first packaging material being gas permeable but the at least second packaging material being impermeable to gases, the creation of a vacuum is possible and, on the other hand, as a result of the first packaging material at the same time being impermeable for microorganisms, the sterility of the interior space of the first packaging and the filter unit enclosed therein can be produced and maintained. The protected filter units according to the invention require less space than conventionally packaged ones, which, in particular, makes storage and postage more cost-effective.

By way of example, medical paper or gas-tight films with a hydrophobic membrane segment can be used as the first packaging material. The medical paper and the hydrophobic membrane segment are gas permeable but are impermeable for microorganisms, in particular bacteria. They therefore have a pore diameter of at most 0.45 µm, preferably at most 0.2 µm. Expediently, the first packaging material is prefabricated in the shape of a tube or a bag. By way of example, gas-tight, flexible plastic films, for example from the group of polyalkenes, preferably polyethylene or polypropylene, can be used as the second packaging material. Such films can also be coated or be composite films, the coating and the composite in particular preventing undesired matter being emitted or evaporated.

In a preferred embodiment of the invention, at least the filter units, together with the interior of the first packaging material which encloses said units, are sterile. In a further preferred embodiment of the invention, the filter units, together with the first packaging material which encloses said units and with at least the interior of the at least second packaging material, are sterile. As a result of these variations, it is possible to react economically to different cleanliness and sterility requirements of the users of the filter units.

The method according to the invention for producing protected filter units for safety filtrations comprises enclosing at least one filter unit in a first flexible packaging material which is gas permeable and impermeable for microorganisms, enveloping at least one enclosed filter unit by at least one second packaging material which is flexible but impermeable to gases except for at least one opening in the envelope, removing gas from the envelope, the first packaging material fixing the at least one filter unit, and closing the at least one opening of the at least second packaging material in a gas-tight fashion.

In a preferred embodiment of the method, a sterilization of the first packaging material with the at least one enclosed filter unit is effected before the step of enveloping. The sterilization can be effected by gassing, for example with ethylene oxide, irradiation with sterilizing beams such as gamma beams or via hot steam treatment, the sterilization preferably being effected by steam. In accordance with a further refinement of the method according to the invention, the protected filter units are subject to a sterilization after the enveloping was carried out. To this end, sterilization is preferably effected by beams, particularly preferably by gamma beams.

It is advantageous that commercially available packaging materials can be used for packing the filter units after said method. The method can be matched to the client's requirements regarding quality, cleanliness and sterility and can easily be automated. As a result of this it is particularly economical.

BRIEF DESCRIPTION OF THE DRAWINGS

FIG. 1 is a schematic cross-sectional view of protected filter unit in accordance with one embodiment of the invention.

DETAILED DESCRIPTION OF THE PREFERRED EMBODIMENT

The invention is now intended to be explained in more detail on the basis of an exemplary embodiment.

Two Sartobran® P 0.2 µm filter candles 10 from Sartorius AG (DE) are bagged in a tube-like Tyvek® bag 12 made of medical paper as first packaging material and the opening of which is sealed in a liquid-tight fashion. The closed Tyvek® bag 12 with the enclosed filter candles 10 is hot steam sterilized for 20 minutes at 134° C. in a hot steam sterilizing chamber. After cooling, three sterilized Tyvek® bags 12 with the enclosed filter candles 10 are bagged in a tube-like bag 16 composed of polyethylene as second packaging material. The three bagged units 12 are transferred to a vacuum welding chamber, evacuated, and the opening 20 of the polyethylene bag is welded in a gas-tight fashion.

Six evacuated, protected filter units 10 for safety filtrations are obtained, which from hot steam sterilized filter candles which are enclosed in a hot steam sterilized bag 12 made of medical paper and which have an outer second packaging 16 from polyethylene film. The packaging materials 12, 16 lie close to the filter candles 10 so that no slip is present between the filter candles 10 and the bags 12, 16 made of medical paper.

The invention claimed is:

1. Protected filter units for safety filtrations comprising a plurality of filter units; a first flexible packaging material that is gas permeable but impermeable for microorganisms, the first flexible packaging material forming a plurality of bags, each of which encloses a plurality of the filter units; and at least a second flexible packaging material that is impermeable to gases and encloses the bags of the first flexible packaging material with the filter units therein, wherein gas is removed from the filter units and areas within the first and second flexible packaging materials so the first and second flexible packaging materials fix the filter units in normal conditions and prevent relative movement between the filter units and the first and second flexible packaging materials, thereby preventing abrasion of the filter units and the first packaging material.

2. The protected filter units as claimed in claim 1, wherein the filter units, together with at least the interior of the first packaging material which encloses said units, are sterile.

3. The protected filter units as claimed in claim 2, wherein the first packaging material is sterile on the outside and at least the interior of the second packaging material is sterile.

4. A method for producing protected filter units for safety filtrations comprising the following steps:
  A enclosing a plurality of filter units in a first flexible packaging material that is gas permeable but impermeable for microorganisms to form a plurality of bags of the first flexible packaging material, with each of the bags having a plurality of the filter units therein,
  B enveloping the bags obtained after step A by at least one second packaging material that is flexible but impermeable to gases to define an envelope with at least one opening,
  C removing gas from the envelope, the first packaging material fixing the filter units, and D closing the at least one opening of the second packaging material in a gas-tight fashion so that the first and second packaging materials fix the filter units and prevent relative movement between the filter units and the first and second packaging materials, thereby preventing abrasion of the filter units and the first packaging material.

5. The method as claimed in claim 4, wherein a sterilization of the first packaging material with the at least one enclosed filter unit is effected before step B.

6. The method as claimed in claim 5, wherein the sterilization is effected as steam sterilization.

7. The method as claimed in claim 4, wherein the protected filter units are subject to a sterilization after step B was carried out.

8. The method as claimed in claim 7, wherein the sterilization is effected as gamma sterilization.

* * * * *